US012734008B2

(12) United States Patent
Batchelor et al.

(10) Patent No.: US 12,734,008 B2
(45) Date of Patent: Sep. 15, 2026

(54) SURGICAL APPARATUS CART HAVING COMMUNICATION CAPABILITIES

(71) Applicant: OLYMPUS MEDICAL SYSTEMS CORP., Tokyo (JP)

(72) Inventors: Kester Julian Batchelor, Mound, MN (US); David M. Leak, Brooklyn Park, MN (US)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 280 days.

(21) Appl. No.: 18/781,089

(22) Filed: Jul. 23, 2024

(65) Prior Publication Data

US 2025/0031950 A1 Jan. 30, 2025

Related U.S. Application Data

(60) Provisional application No. 63/516,032, filed on Jul. 27, 2023.

(51) Int. Cl.
*A61B 50/13* (2016.01)
*A61B 1/00* (2006.01)

(52) U.S. Cl.
CPC .......... *A61B 50/13* (2016.02); *A61B 1/00011* (2013.01); *A61B 1/00059* (2013.01); *A61B 1/00147* (2013.01)

(58) Field of Classification Search
CPC ............ A61B 1/00147; A61B 1/00011; A61B 1/00059; A61B 50/13; G16H 20/40; G16H 40/20; G16H 40/63; G16H 40/67
See application file for complete search history.

(56) References Cited

U.S. PATENT DOCUMENTS

| | | | | |
|---|---|---|---|---|
| 7,654,261 | B1 * | 2/2010 | Rockhold | A61B 50/13 128/202.13 |
| 2009/0267772 | A1 * | 10/2009 | Dehnadi | G07F 9/026 340/572.8 |
| 2013/0248598 | A1 * | 9/2013 | Dehnadi | G07F 9/026 235/385 |
| 2023/0285614 | A1 * | 9/2023 | Kotani | A61B 1/00 |
| 2023/0285615 | A1 * | 9/2023 | Kotani | A61B 1/121 |

FOREIGN PATENT DOCUMENTS

| | | |
|---|---|---|
| CN | 215384631 U | 1/2022 |
| JP | 2009219700 A | 10/2009 |

* cited by examiner

*Primary Examiner* — Thomas Randazzo
(74) *Attorney, Agent, or Firm* — Schwegman Lundberg & Woessner, P.A.

(57) ABSTRACT

A supply cart includes a transceiver, a processor, at least one sensor and at least one indicator. A transceiver receives endoscope procedure data from a server. A processor is configured to read the endoscope procedure data and determine an instrument and one or more consumables needed for a procedure associated with the endoscope procedure data. At least one sensor is configured to determine a presence or absence of the instrument at the supply cart. At least one indicator is configured to provide an indication relating to the presence or the absence of the instrument at the supply cart.

20 Claims, 10 Drawing Sheets

SURGICAL APPARATUS CART HAVING COMMUNICATION CAPABILITIES

RELATED APPLICATION DATA

This application is based on and claims priority under 35 U.S.C. § 119 to U.S. Provisional Application No. 63/516,032, filed on Jul. 27, 2023, the entire contents of which are incorporated herein by reference.

TECHNICAL FIELD

This document pertains generally, but not by way of limitation, to a supply cart to hold instruments and consumables for use during a surgical procedure.

BACKGROUND

A surgical cart provides storage for and easy access to instruments during a surgical procedure. The surgical cart can keep the instruments sterile and organized such that a practitioner can easily access an instrument, thereby minimizing distractions that can occur. Furthermore, surgical carts can assist personnel with keeping track of inventory levels.

Before a surgical procedure, such as a preparation phase of an endoscopic procedure, personnel must ensure that the surgical cart has the proper instruments. The personnel must also ensure that the surgical cart includes the necessary consumables for the endoscopic procedure. This can include tubes, clips, forceps, guidewires, needles, and the like. If a proper instrument is not on the surgical cart, or if the surgical cart does not include the proper consumables, this can increase the time associated with the surgical procedure if this determination is not made until the surgical procedure is underway.

SUMMARY

Accordingly, what is needed is a supply cart that can determine whether or not the supply cart includes a transceiver receiving endoscope procedure data from a server; a processor configured to read the endoscope procedure data and determine an instrument and one or more consumables needed for a procedure associated with the endoscope procedure data; at least one sensor configured to determine a presence or absence of the instrument at the supply cart; and at least one indicator configured to provide an indication relating to the presence or the absence of the instrument at the supply cart.

In some instances, the supply cart can be used for a plurality of upcoming procedures where the data received from the centralized server can include various instruments and consumables that should be available at the supply cart for the upcoming procedures. A first upcoming procedure of the plurality of upcoming procedures can require a first instrument and one or more first consumables (e.g., a first set of consumables) while a second upcoming procedure of the plurality of upcoming procedures can require a second instrument different from the first instrument along with one or more second consumables (e.g., a second set of consumables). Here, the first and second sensors can be used to inform a practitioner if the supply cart is ready for the plurality of upcoming procedures or if instruments and/or consumables need to be added to the supply cart.

The supply cart can determine a location at which the supply cart is located and transmit location information corresponding to the location to the centralized server. The supply cart can also receive data relating to a practitioner who is to utilize the supply cart during an upcoming procedure, determine when the practitioner is proximate to the supply cart, and provide indicia, such as illuminating a light source, when the practitioner is proximate to the supply cart. Thus, the practitioner can easily locate the supply cart.

Once a procedure is complete, the second sensors can be used to determine what consumables were used during the procedure. This data can be supplied to a processor of the supply cart, which can be transmitted to the centralized server. The centralized server can use this data to reorder the consumables. Furthermore, the centralized server can use this data for billing purposes, such as billing a patient associated with the procedure for which the consumables were used.

A potential advantage includes quickly determining what instruments and consumables are present and need to be added to a supply cart for upcoming procedures.

Another potential advantage relates to easily locating a supply cart in an area that stores a plurality of supply carts.

A further potential advantage includes automating reordering of consumables after a procedure is performed.

BRIEF DESCRIPTION OF FIGURES

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

A supply cart can receive data from a centralized server and transmit data to the centralized server. The data can relate to the upcoming procedure where various instruments and consumables should be available at the supply cart for the upcoming procedure. The supply cart can include first sensors which can provide information relating to the presence or absence of the various instruments needed for the upcoming procedure. The supply cart can also include second sensors which can provide information relating to the presence or absence of consumables along with an amount of the consumables that should be available for the upcoming procedure. Based on information provided by the first and second sensors, a practitioner can quickly determine if the supply cart is ready for the upcoming procedure or if instruments and/or consumables need to be added to the supply cart. A practitioner could be a doctor, a runner for a specific operating room, a scrub technician, or the like.

Figure 1:
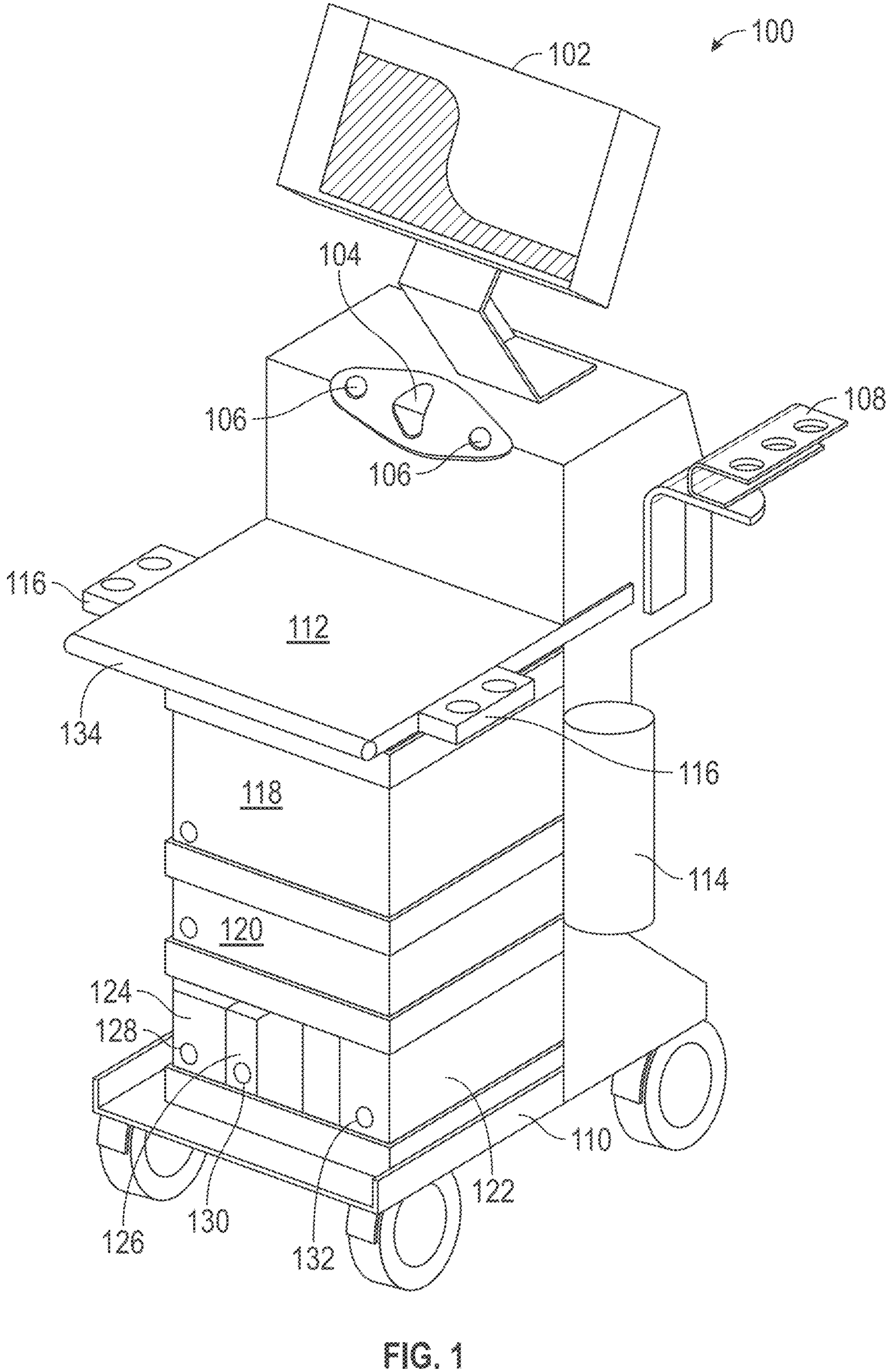
FIG. 1 illustrates a perspective view of a smart cart that can be used to supply instruments and consumables during a procedure, in accordance with examples.
Figure 2:
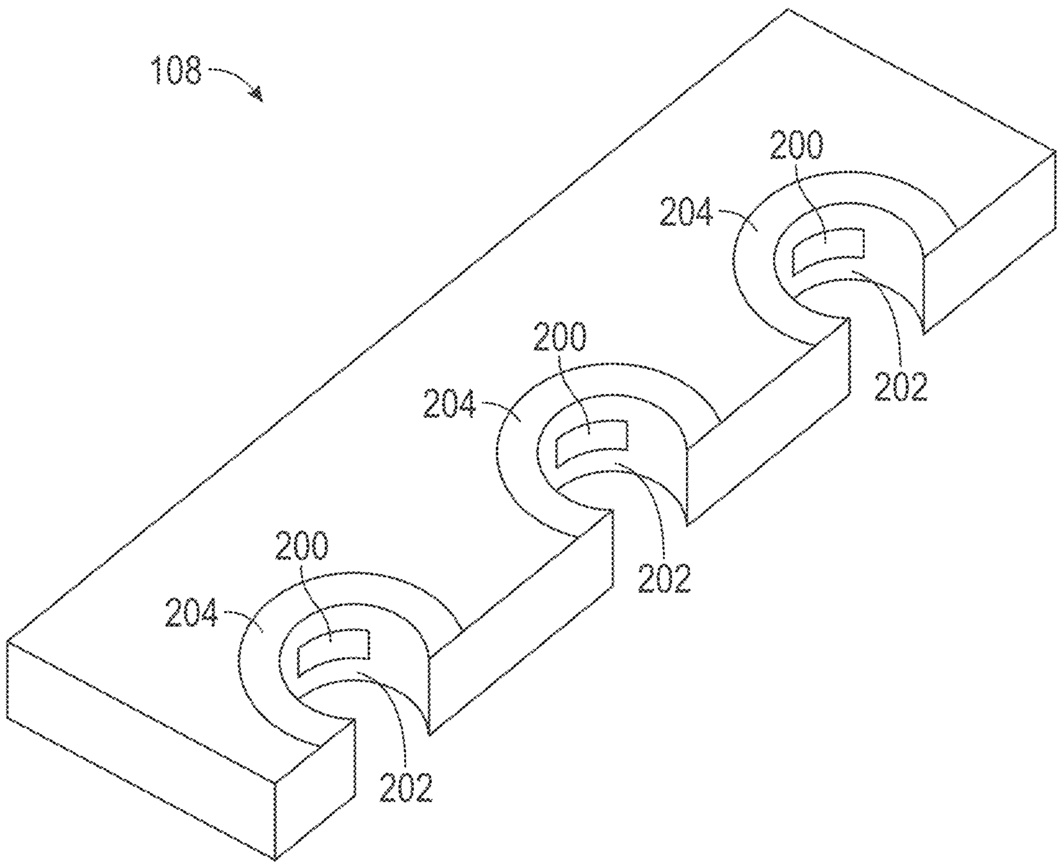
FIG. 2 illustrates an endoscope instrument hanger of the smart cart of FIG. 1, according to some examples.
Figure 3A:
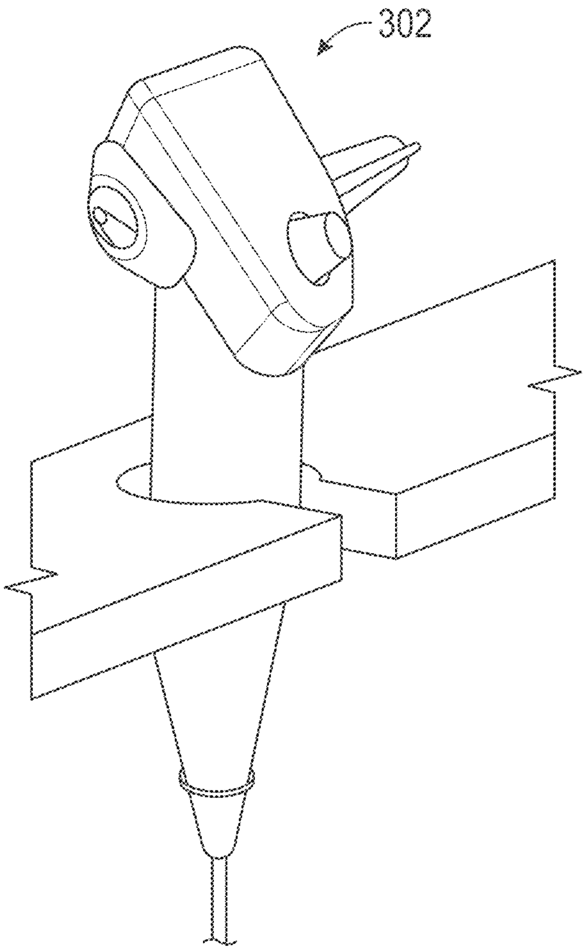
FIG. 3A illustrates an example of an instrument disposed within the endoscope instrument hanger of FIG. 2, according to some examples.
Figure 3B:
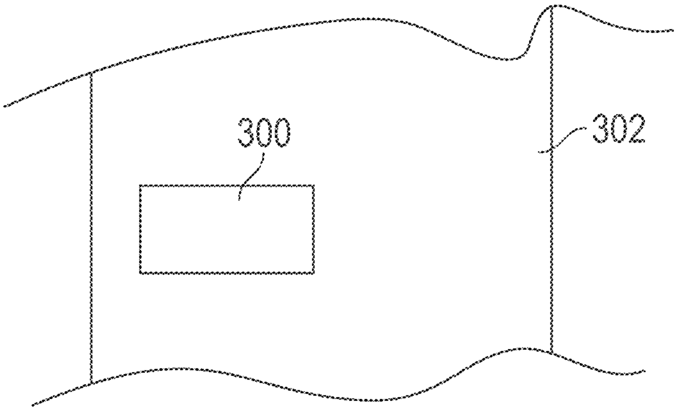
FIG. 3B illustrates a label of the instrument in FIG. 3A, according to some examples.
Figure 4:
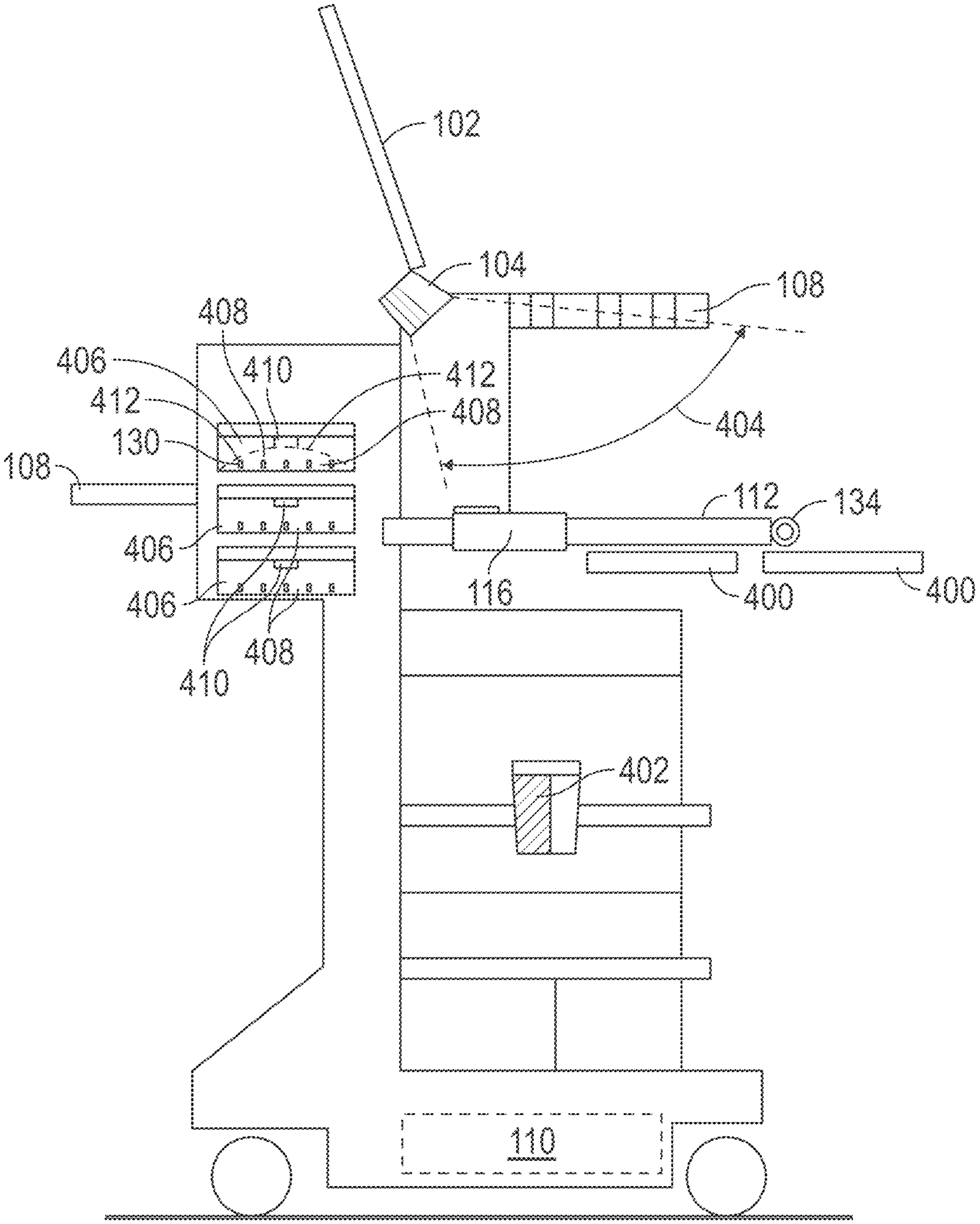
FIG. 4 illustrates a side view of the smart cart of FIG. 1, according to some examples.
Figure 5:
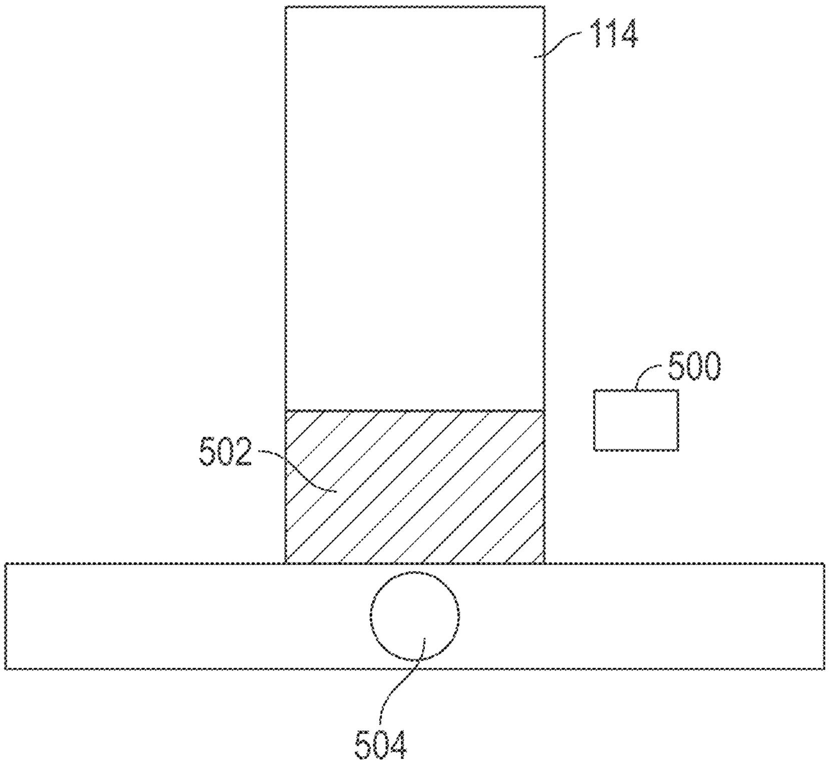
FIG. 5 illustrates a sensor that may be used to assist with determining characteristics of a consumable disposed within an accessory, according to some examples.
Figure 6:
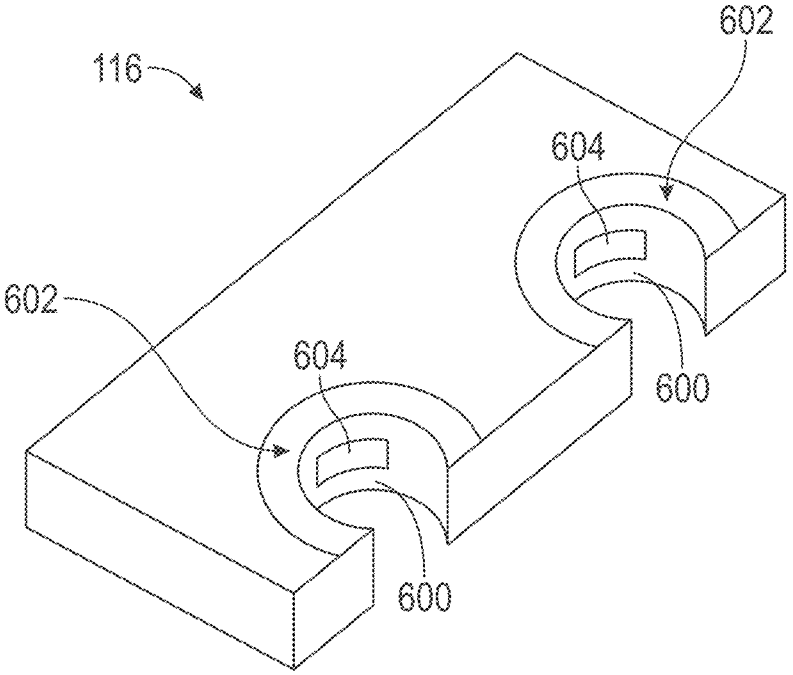
FIG. 6 illustrates accessory shelving of the smart cart of FIG. 1, according to some examples.
Figure 7:
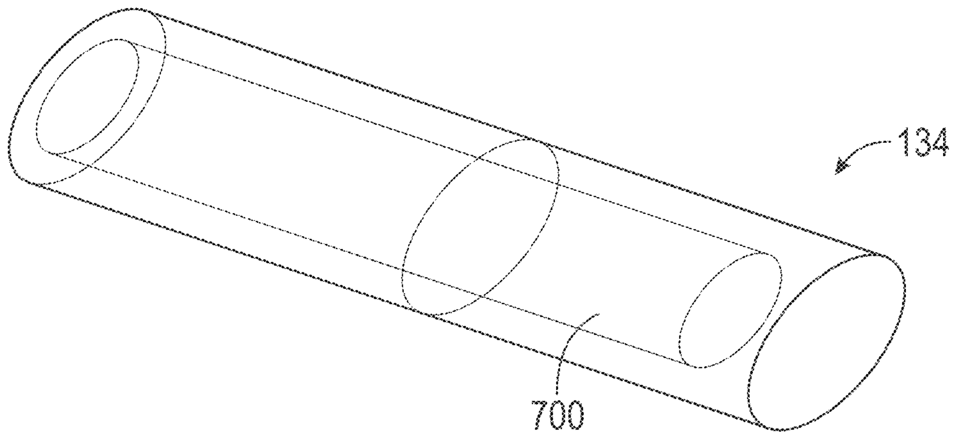
FIG. 7 illustrates a handle of the smart of FIG. 1, where the handle includes a lighting feature, according to some examples.

FIG. 1 is a perspective view of a smart cart 100, which can store instruments and consumables that can be used during a procedure. As the smart cart 100 can store instruments and consumables, the smart cart 100 can be a supply cart. The smart cart 100 can include a display 102 along with a camera 104 and speakers 106. The display 102 can be any type of display device, such as a light emitting diode (LED) display, a liquid crystal display (LCD), a plasma display, or the like. The display 102 can output data from instruments used during a procedure. The display 102 can also display output data from sensors communicatively coupled with the smart cart 100, as will be described further on. The camera 104 can be any type of image capturing device capable of capturing and recording a field of view. The speakers 106 can be any type of audio device capable transmitting any type of audio signals, such as audio alerts, or the like.

The smart cart 100 can also have an instrument hanger 108, which can be an endoscope instrument hanger, a work surface 112, and an accessory 114. Herein, the term accessory 114 will be interchangeable with the term accessories 114. Thus, any reference to the term accessory 114 is applicable to the term accessories 114 and vice versa. The instrument hanger 108 can be used to hold instruments that can be used during a procedure. Instruments that can be held within the instrument holder 108 can include endoscopes, hysteroscopes, laryngoscopes, bronchoscopes, or any other type of instrument or tool that can be used during any type of procedure. The instrument hanger 108 can include a sensor (first sensor) 200 that can determine the presence or absence of an instrument within instrument receptacles 202 of the instrument hanger 108, The sensor 200 can be a radio frequency identification (RFID) scanner, a barcode scanner, a near-field communication (NFC) reader, or any other type of wireless short range wireless communication sensor that can read a tag 300 on an instrument 302. The sensor 200 can determine if the instrument 302 has been sterilized. In particular, the instrument 302 could include an RFID chip where sterilization information could be written to the RFID chip and read by the sensor 200. The information could relate to the sterilization status of the instrument 302, such as if the instrument 302 has been sterilized or if the instrument 302 has not been sterilized.

When the instrument 302 is placed in the instrument receptacle 202, the sensor 200 can read the tag 300. The tag 300 can include data relating to the instrument 302, such as the type of the instrument 302, a power level of the instrument 302, a life span of the instrument 302, whether or not the instrument 302 has been sterilized, a model number of the instrument 302, or any other type of data. The sensor 200 can read data from the tag 300 and relay the data to a cart controller 110 of the smart cart 100 via Bluetooth, NFC, or any other type of short-range wireless communication medium. The sensor 200 can also relay the data to the cart controller 110 via a wired connection.

The instrument hanger 108 can have an indicator (first indicator) 204, which can provide indicia relating to the instrument 302 within the instrument receptacle 202. The indicator 204 can be a LED, which can emit different colors based on the presence or absence of an instrument within the instrument receptacle 202. Furthermore, if the instrument 302 is disposed within the instrument receptacle 202, the indicator 204 can emit light at different colors based on a condition of the instrument 302 or various other factors, such as if the instrument 302 is not suitable for an upcoming procedure. To further illustrate, if the power level of the instrument 302 is low, the indicator 204 can emit light having a red color to indicate that the instrument 302 is not suitable for an upcoming procedure. In addition, if the instrument 302 is reaching the end of its lifespan, the indicator 204 can emit light having a red color to indicate that the instrument 302 is not suitable for an upcoming procedure. Moreover, if a practitioner is performing a procedure that requires an endoscope and the practitioner has a certain preference for a particular type of endoscope, which is not the instrument 302, the indicator 204 can emit light having a red color to indicate that the instrument 302 is not suitable for an upcoming procedure. Similarly, if the instrument 302 disposed within the instrument receptacle 202 is suitable for the upcoming procedure, the indicator 204 can emit light having a green color to indicate that the instrument 302 is suitable for the upcoming procedure. The information conveyed by the indicator 204 can be determined when the sensor 200 reads the tag 300. The instrument 302 can wirelessly communicate with the display 102 output information gleaned from the instrument 302 during a procedure.

The workspace 112 can be used by a practitioner, which can be used in conjunction with an input device 400 and an accessory 402, The accessories 114 and 402 can be vessels that can be used during a procedure, such as gas sources, including carbon dioxide or oxygen, fluid sources, or any other types of materials that could be used or provided to a patient during a procedure. The input device 400 can be a keyboard or tablet, that can allow a user to interact with the display 102 and the cart controller 110.

In examples where the accessories 114 and 402 store materials, such as when the accessories are vessels, the accessories 114 and 402 can include a sensor (a second sensor) 500 that can determine a quantity and a type of material disposed within the accessories 114 and 402. If the accessory 114 is a vessel storing a fluid 502, the sensor 500 can have functionality similar to the camera 204 discussed above and measure a level of the fluid within the accessory 114 and relay the fluid level along with data pertaining to the fluid itself to the cart controller 110. The data forwarded by the sensor 500 to the cart controller 110 can include an image of the fluid within the accessory 114. The cart controller 110 can have a spectrometer that can analyze an image provided by the sensor 500 to determine a type of fluid such that the cart controller 110, via the display 102, can indicate to a practitioner if the smart cart 100 has the proper consumables for an upcoming procedure, where appropriate, based on an image captured by the sensor 500 of the fluid 502. Additionally, the smart cart 100 can include an indicator (a second indicator) 504, which can be similar to the indicator 204, which can provide indicia relating to the fluid 502 to a practitioner indicating whether or not the smart cart 100 has the proper consumables for an upcoming procedure.

The camera 104 can also be used to determine if the smart cart 100 comprises the instruments 302 and consumables for an upcoming procedure. The camera 104 can create a field of view 404 that can encompass the instrument hanger 108 and accessories shelving (an accessories shelf) 116. When the instruments 302 are disposed within the instrument hanger 108, the camera 104 can detect and read the tags 300 as detailed above with reference to the sensor 200 and provide data relating to the instrument 302 as detailed above with reference to the sensor 200. Thus, in addition to the sensor 200, the camera 104 can be used to determine the presence of the proper instruments for an upcoming procedure.

The accessories shelving 116 can be used to store consumables and accessories for the smart cart 100. The consumables and accessories can include tubing sets, white panel cups, a barcode reader, a portable RFID scanner, a white light balancing cup, and any other accessories that can be used during a surgical procedure. Consumables can further include items such as gloves, gowns, gauze, bandages, masks, surgical drapes, or the like. The accessory shelving 116 can include accessory receptacles 600 to hold accessories along with indicators 602. The indicator 602 can be similar to the indicator 204 as discussed above and can provide indicia relating, to accessories within the accessory receptacle 600. The accessory receptacles 600 can have a sensor 604 that can determine the presence or absence of accessories or consumables within the accessory receptacles 600. The sensor 604 can be similar to the sensor 200 as discussed above. Thus, the sensor 604 can provide data to the cart controller 110.

The smart cart 100 can also include apparatuses 118 and 120. The apparatuses 118 and 120 can function to process image signals received from the instrument 302 and output an image signal to the display 102. Alternatively, the apparatuses 118 and 120 could individually or collectively provide a light source for the instrument 302. Moreover, the apparatuses 118 and 120 could include an energy platform, such as an ultrasonic device, an RF device, a laser, a cold plasma device, an insufflation source, an argon plasma unit, an ultrasound device, or the like.

The smart cart 100 can comprise devices 122 and 124 and a container 126. The devices 122 and 124 can provide various functionalities for the smart cart 100, such as a pump for the accessories 114 and 402, a controller for the accessories 114 and 402, and the like. The container 126 can store materials that can be used during a procedure, such as water, saline, or any type of gas. Moreover, the devices 122 and 124 can be vacuum pumps that can provide a vacuum for the instrument 302.

The devices 122 and 124 can include sensors 128 and 130, which can function to determine a functional state of each of the devices 122 and 124. The functional state can include a power level of the devices of 122 and 124, a life span of the devices 122 and 124, model numbers of the devices 122 and 124, or a vacuum status of the devices 122 and 124 in instances when one or both of the devices 122 and 124 function as vacuum pumps. The functional state can include any other type of information relating to the devices 122 and 124 that the cart controller 110 can use to determine if the devices 122 and 124 are suitable for upcoming procedures that the smart cart 100 will be used for. The sensors 128 and 130 can be similar to the sensor 200 as discussed above and provide data to the cart controller 110 in a similar manner as the sensor 200.

The container 126 can include a sensor 132, which, similar to the sensor 500, can determine a quantity and a type of material disposed within the container 126. If the container 126 is a vessel storing a fluid, the sensor 132 can have functionality similar to the camera 204 discussed above and measure a level of the fluid within the container 126 and provide this data to the cart controller 110. The cart controller 110 can process the data to determine a type of the fluid and other characteristics of the fluid as detailed above.

The smart cart 100 can also include drawers 406, which can store consumables, such as tubes, clips, forceps, guidewires, needles, and the like, within bins 408. The drawers 406 can have a rectilinear configuration in order to allow for the secure storage of consumables therein. The bins 408 can be formed from walls that project from a bottom surface of the drawers 406 in order to create divided portions within the drawer 406. Different consumables can be stored within different ones of the bins 408 in the drawers 406.

Sensors 410 can be disposed within the drawers 406 and can determine an amount of consumables within the bins 408. The sensors 410 can have the configuration of the camera 104 or the sensors 200. When the sensors 410 have the configuration of the camera 104, the sensors 410 can create a field of view 412 to identify the type and amount of consumables that are present in the bins 408. The sensors 410 can relay this information to the cart controller 110 in a manner similar to that discussed above with reference to the sensors 200.

When the sensors 410 have the configuration of the sensors 200, the consumables can include tags, such as the tags 300, and can include information relating to the consumables. This information can include an identification of the consumables, a manufacture date of the consumables, product information about the consumables, such as dimensions and materials, or the like. The sensor 410 can read this information from the tags and relay this information to the cart controller 110 as discussed above with reference to the sensor 200.

The smart cart 100 can be stored with a plurality of other smart carts, therefore making quick identification of a smart cart identified to be used for an upcoming procedure time consuming. The smart cart 100 can include a handle 134 that can be formed of a transparent material and illuminated with a lighting feature 700 to indicate to a practitioner that the smart cart 100 having the illuminated handle 134 should be selected by the practitioner. The lighting feature 700 can be a LED, a halogen light bulb, a fluorescent light bulb, an incandescent light bulb, or any other type of illuminating device, that can be powered by the cart controller 110.

Figure 8:
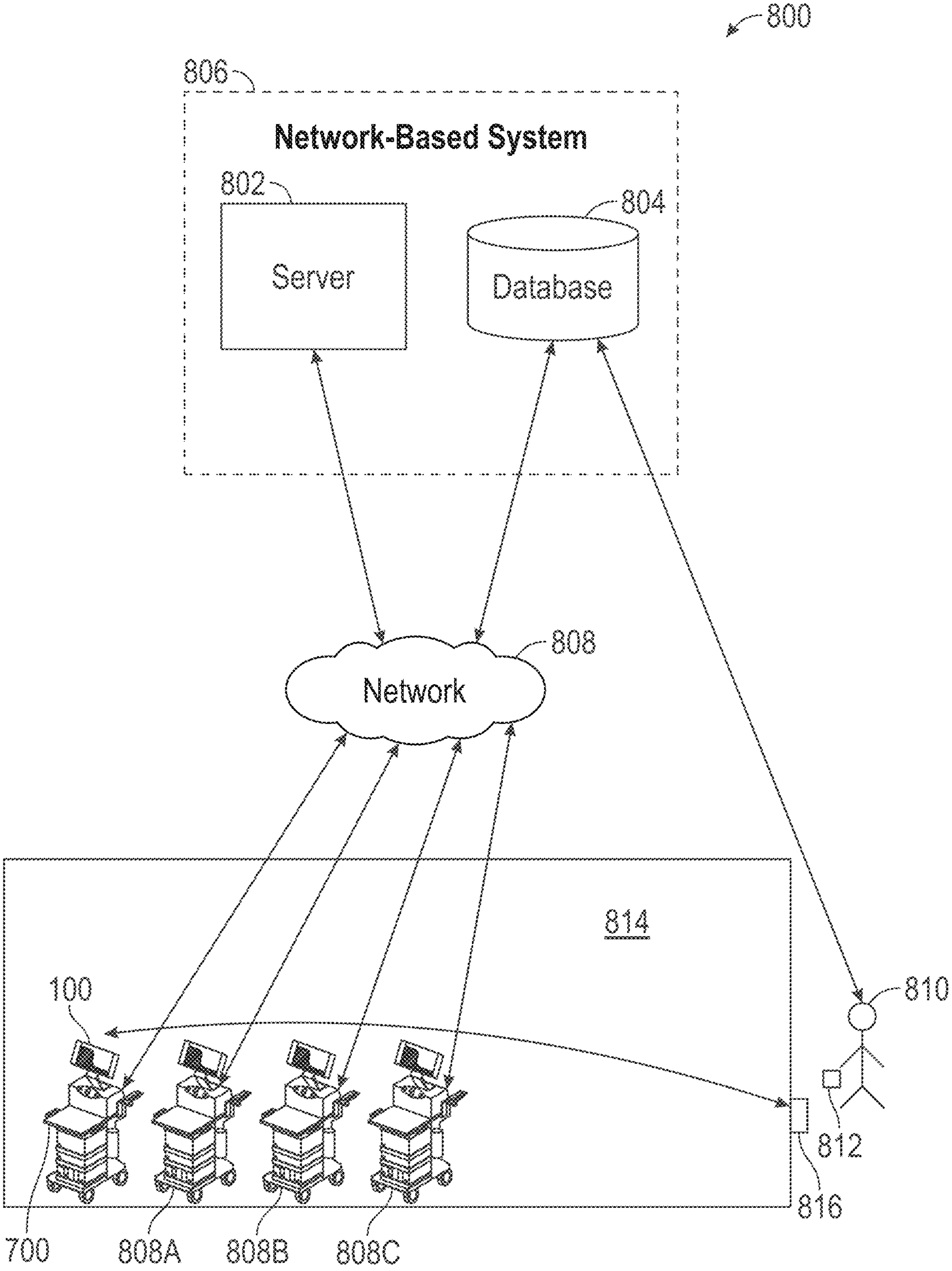
FIG. 8 illustrates a network diagram illustrating a network environment within which the smart cart of FIG. 1 can operate, according to some examples.

FIG. 8 is a network diagram illustrating a network environment 800 within which the smart cart 100 can operate, according to some examples. The network environment 800 can include a server 802 along with a database 804 where the server 802 and the database 804 can be part of a network-based system 806. The network-based system 806 can be at a facility where medical procedures are performed. The server 802 or the database 804 or both the server 802 and the database 804 can store upcoming endoscopic procedures that will be performed along with a smart list of what smart carts, such as the smart carts 100 and 808A-808C, are assigned to each of the upcoming procedures.

The smart list can be used to select which of the smart carts 100 and 808A-808C to select for the upcoming procedures. The smart list can include endoscope procedure data that lists what instruments, such as the instruments 320, along with what accessories, such as tubing sets at the accessories shelving 116, are necessary for each of the upcoming procedures. The endoscope procedure data can also include practitioner preferences. Thus, if a practitioner has a preference for a certain type of instrument, such as a certain type of endoscope, the endoscope procedure data can reflect this preference. The smart list can also include, in instances where the accessories 114 and 402 are vessels, an amount of fluid or gas, such as saline, carbon dioxide, or oxygen, necessary for the upcoming procedures along with a type and amount of additional consumables, such as a type and amount of guidewires and needles, that are necessary for upcoming procedures. The smart lists stored at the server 802 and the database 804 can include other types of information for upcoming endoscope procedures in addition to that disclosed herein. As will be discussed further on, the cart controller 110 can store a procedure list, which can indicate which consumables should be used with a particular procedure.

The network environment 800 can include a network 808 that can facilitate communication between the server 802 and the smart carts 100 and 808A-808C and the database 804 and the smart carts 100 and 808A-808C. The network 808 can be any network that enables communication between or among machines, databases, and devices. Accordingly, the network 808 can be a wired network, a wireless network (e.g., a mobile or cellular network), or any suitable combination thereof. The network 808 can include one or more portions that constitute a private network, a public network (e.g., the Internet), or any suitable combination thereof. Thus, the network 808 can include a local area network (LAN), a wide-area network (WAN), or the like.

Figure 9:
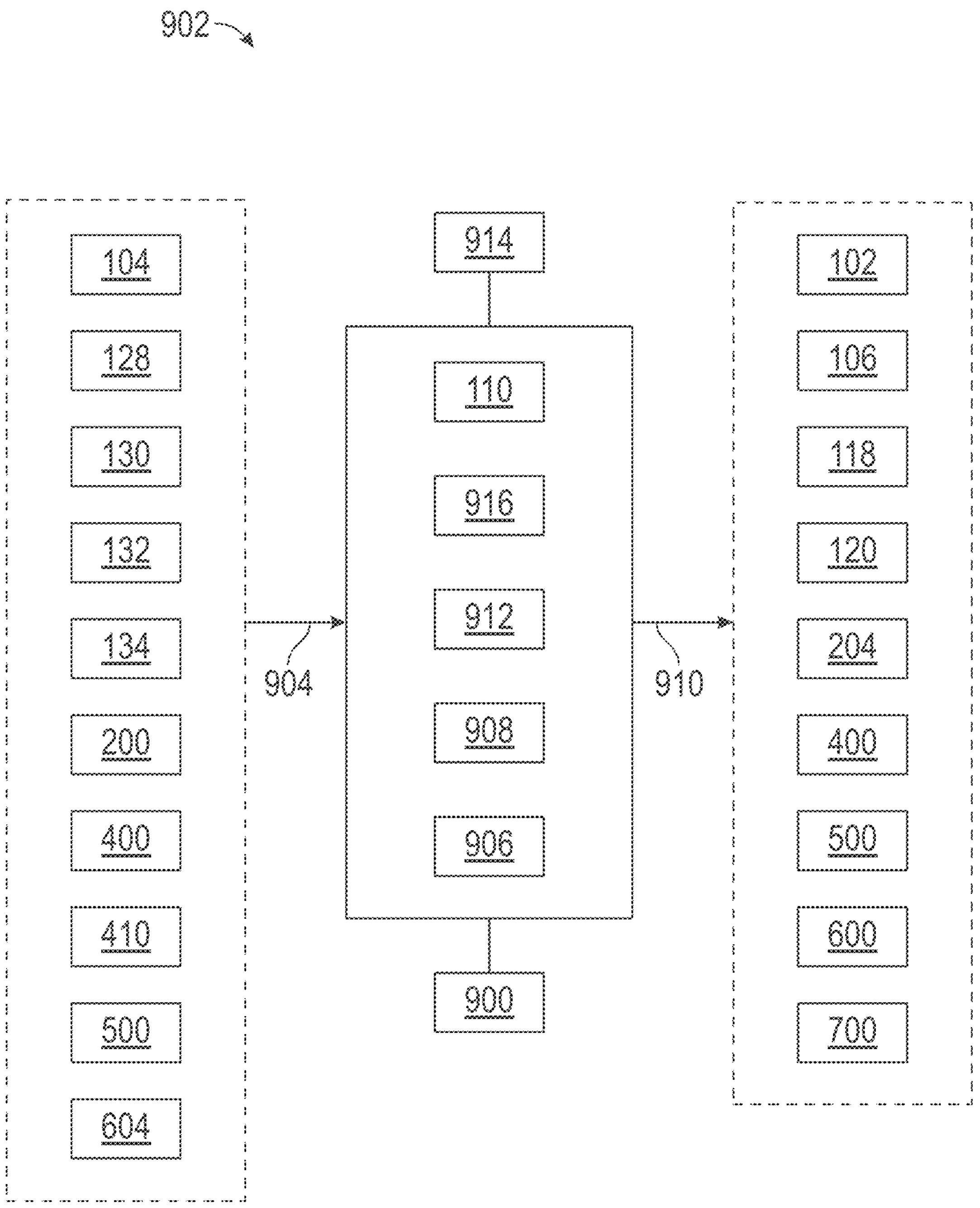
FIG. 9 illustrates a system diagram of the smart cart of FIG. 1, according to some examples.
Figure 10:
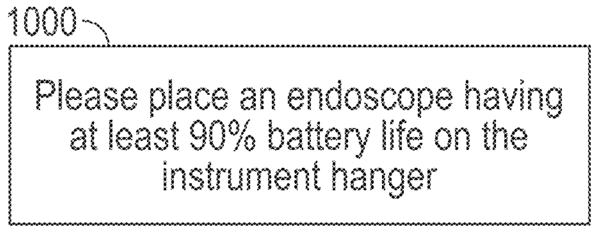
FIGS. 10 and 11 illustrate user interfaces that are shown on a display of the smart cart of FIG. 1, according to some examples.
Figure 11:
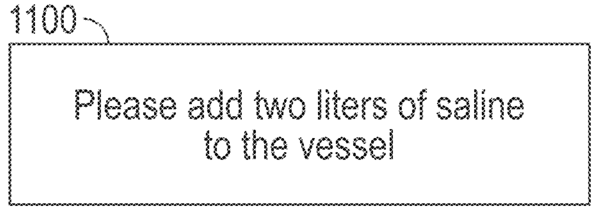
Figure 12:
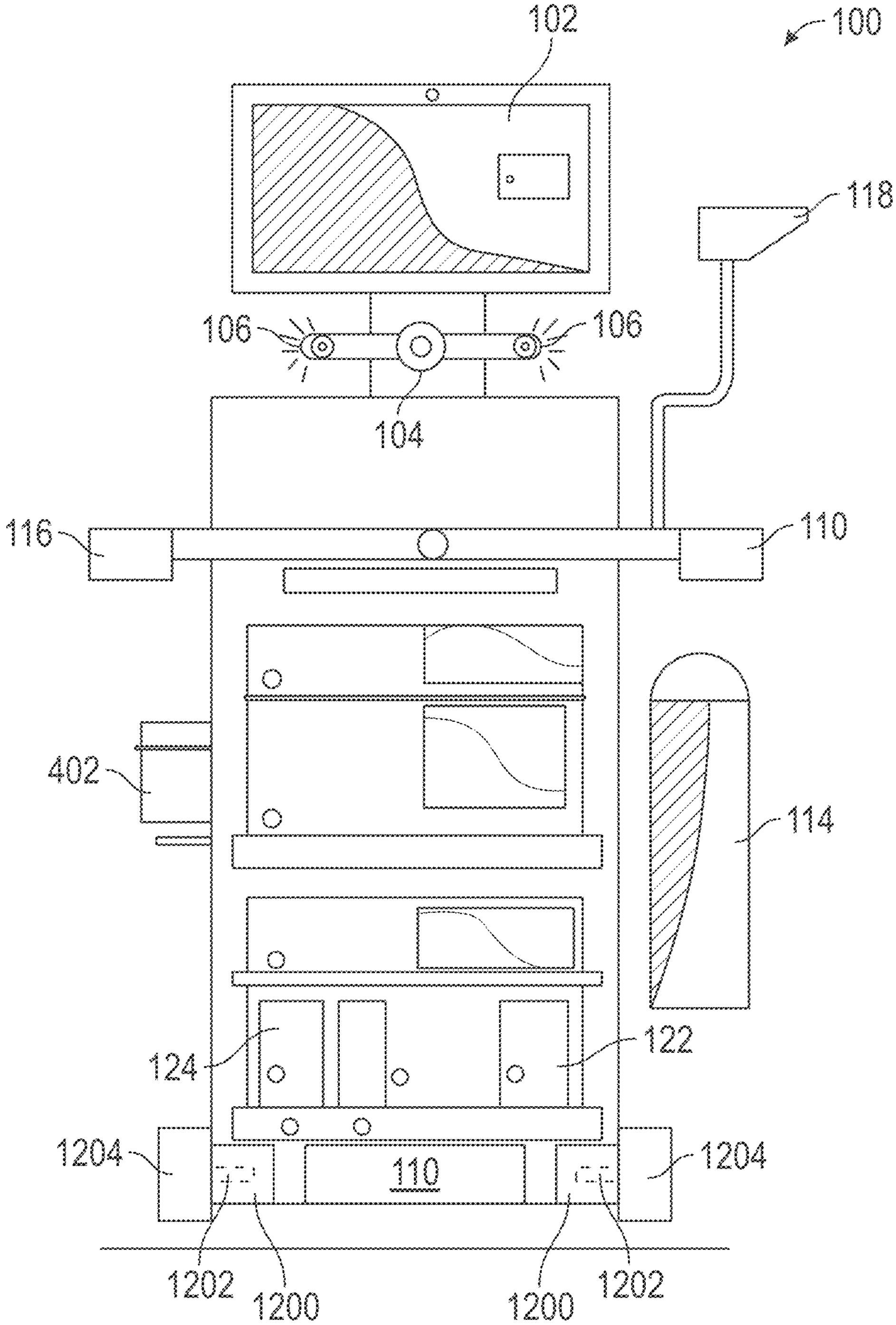
FIG. 12 illustrates a front view of the smart cart of FIG. 1, according to some examples.

The smart carts 100 and 808A-808C can include a transceiver 900, which can facilitate communication between the smart carts 100 and 808A-808C and the server 802 and the database 804, as shown in FIG. 9, which is a system diagram 902 of the smart cart 100. The transceiver 900 can be any type of electronic device that can include a wired or wireless transmitter and a wireless receiver each capable of communicating with the server 802 and the database 804, either directly or via the network 808. Thus, the transceiver 900 can receive endoscope procedure data from the server 802 and the database 804 relating to upcoming procedures.

The cart controller 110 can also have a processor 906 and memory 908 where the processor 906 can read and interpret the data received from the transceiver 900, such as endoscope procedure data. The processor 906 can be a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application-Specific Integrated Circuit (ASIC), a Radio-Frequency Integrated Circuit (RFIC). In addition, the processor 906 can include multi-core processors that may comprise two or more independent processors (also referred to as "cores") that may execute instructions contemporaneously. The processor 906 can read the endoscope procedure data received by the transceiver 900 and determine what instruments and consumables are necessary for the upcoming procedures.

The system diagram 902 illustrates which elements of the smart cart 100 provide inputs to the cart controller 110 and which elements receive an output from the cart controller 110. As discussed above, the camera 104 along with each of the sensors 128-132, 200, 410, 500, and 604 can provide data to the cart controller 110. The input device 400 can also provide data to the cart controller 110. This data can be provided to the cart controller 110 as input 904. The camera 104 along with each of the sensors 128-132, 200, 410, 500, and 604 can passively provide the input 904 or actively provide the input 904 in response to a request from the cart controller 110.

In a passive mode, the input 104 can be provided to the cart controller 110 on a periodic basis. Thus, the smart cart 100 can self-identify the contents stored thereon. In an active mode, the cart controller 110 can prompt the camera 104 along with the sensors 128-132, 200, 410, 500, and 604 to provide the input 904. In particular, when the server 802 or the database 104 send endoscope procedure data, the cart controller 110 can activate the camera 104 along with each of the sensors 128-132, 200, 410, 500, and 604 to determine if the smart cart 100 has the proper instruments and consumables for the upcoming endoscope procedures. The cart controller 110 can make this determination by comparing the input 904 with the endoscope procedure data received from the processor 906. The determination can also be made based on the preferences of a practitioner. Thus, if a practitioner prefers a certain type of endoscope, the cart controller 110 can determine not only whether the smart cart 100 includes an endoscope, but whether or not the smart cart 100 has an endoscope preferred by a practitioner who will be using instruments stored on the smart cart 100. Moreover, the cart controller 110 can determine if the instruments and the consumables are in a proper state based on the procedure data and if the smart cart 100 has the proper amount of consumables.

The cart controller 110 can provide outputs 910 to the display 102, the speakers 106, the consoles 118 and 120, the indicators 204, 504, and 602, the input device 400, and the light 700, For the outputs 910 provided to the display 102, the indicators 204, 504, and 602, the input device 400, and the light 700, the cart controller 110 can provide the outputs based on the endoscope procedure data received from the server 802 and the inputs 904. The cart controller 110 can also include a power source 916, which can be a battery, such as a Nickel Cadmium battery, a Lithium Ion battery, or any other type of battery. In addition, the smart cart can receive power from an external power source that can couple with the power source 914.

In an example, referred to herein as the "first example," the procedure data indicates an ultrasonic probe is required for an upcoming procedure and the instrument hanger 108 includes a hysteroscope. As such, the cart controller 110 can cause the indicator 204 to illuminate red via the output 910. Furthermore, the cart controller 110 can cause a user interface 1000 to be displayed at the display 102 that prompts a user to place an ultrasonic probe having a battery life of at least 90% (for example) on the instrument hanger 108. The user interface 1000 can also be displayed on the input device 400.

In the first example, the upcoming procedure also requires two gallons (for example) each of saline and water, which will be reflected in the procedure data. Thus, the sensors 500 can provide the input 904 to the cart controller 110 regarding fluid types and fluid levels in the accessories 114 and 402. The cart controller 110 can include an analyzer 912, such as a spectrometer, which can analyze the data received from the sensors 500 and determine that the accessory 114 has water and the accessory 402 has saline. Moreover, the sensor 500 can provide a fluid level with the input 904, which in the first example corresponds to three gallons for both saline and water. As a result, the cart controller 110 can send a signal to the indicator 504 causing the illumination of a green LED.

The smart cart 100 can also include localization circuitry 914, which can be used to determine a location of the smart cart 100. The localization circuitry 914 can also create location data based on the location of the smart cart 100 and provide the location data to the transceiver 900 for transmission to the server 802. The localization circuitry 914 can include a global position system (GPS) that can determine a location of the smart cart 100. In addition, the localization circuitry 914 can use an indoor positioning system where radio frequency patterns from Wi-Fi access points located throughout a facility within which the smart cart 100 is located are used to determine the location of the smart cart 100. The localization circuitry 914 can periodically provide the server 802 with location updates.

In a second example, referred to herein as the "second example," the server 802 can determine that the smart cart 100 should be used with two separate upcoming procedures where a first procedure will require a bronchoscope and the second procedure will require a hysteroscope. Moreover, the first procedure will be performed in operating room "A" and the second procedure will be performed in operating room "B.". In the second example, the consumables needed for the first procedure include water, saline, and needles. For the second procedure, the consumables needed for the second procedure include water, saline, and tubing. In the second example, the smart list indicates that the smart cart 100 should be assigned to a user 810 during the first and second procedures.

In the second example, the server 802 can transmit endoscope procedure data to the smart cart 100. In addition, the server 802 can transmit location information relating to the smart cart 100 to a user device 812, such as a mobile cellular device having Wi-Fi capabilities. In the second example, the localization circuitry 914 previously sent location data to the server 802 indicating that the smart cart 100 is located in an area 814, which also includes the smart carts 808A-808C. The server 802 transmits this location data to the user device 812.

In the second example, the cart controller 110 can prompt the camera 104 along with each of the sensors 128-132, 200, 410, 500, and 604 to provide data regarding the instruments and consumables currently disposed at the smart cart 100, In response, the camera 104 can provide as the input 904 that the instrument hanger 108 includes a bronchoscope and a hysteroscope. Thus, the cart controller 110 can cause the indicator 204 to illuminate green via the output 910. Furthermore, the sensors 500 can provide the input 904 to the cart controller 110 regarding fluids in the accessories 114 and 402. The analyzer 912 can determine that the accessory 114 has water and the accessory 402 has saline. Moreover, the sensor 500 can provide a fluid level with the input 904, which in the second example corresponds to the amount of water necessary for both of the upcoming procedures that the smart cart 100 will be used for. Thus, the cart controller 110 can send a signal to the indicator 504 causing the illumination of a green LED that is associated with the accessory 114. However, when the sensor for the accessory 402 determines that the fluid level for the saline is below a threshold amount necessary for both of the upcoming procedures, the cart controller 110 can send a signal to the indicator 504 causing the illumination of a red LED that is associated with the accessory 114. Additionally, the cart controller 110 can cause a user interface 1100 to be displayed at the display 102 that can prompt a user to add two liters of saline to the accessory 402, which in the second example is a vessel thereby showing the absence of consumables at the smart cart 100, The user interface 1100 can also be displayed on the input device 400.

The user 810 can be assigned to the smart cart 100 in the second example. When the user 810 arrives at the area 814 and scans their identification badge via their user device 812 at a scanner 816 to gain entrance to the area 814, the scanner 816 can transmit information, such as object data, to the transceiver 900, indicating that the user 810 is proximate the smart cart 100. When the transceiver 900 receives information that the user 810 is proximate the area 814, the transceiver can send a signal to the cart controller 110, which can cause illumination of the lighting feature 700, Accordingly, the user 810 can easily find the smart cart 100 upon entering the area 814. The cart controller 110 can also cause the speaker 106 to emit an audible tone thereby providing an indication to the user 810 of the location of the smart cart 100. Moreover, the first procedure is set to occur in operating room A. Thus, when the user 810 touches the handle 134, the handle can provide the input 904 to the cart controller 110, which can cause a prompt to be put on the display 102 indicating that the smart cart 100 should be moved to the operating room A for the first procedure. In addition, the cart controller 110 can cause a prompt to be put on the display 102 indicating that the smart cart 100 should be moved to the operating room B for the second procedure.

The camera 104 along with the sensors 500 and 604 can assist with patient billing. After the smart cart 100 has been used during a procedure, each of the accessories 114 and 402, the accessory receptacles 600, the camera 104, and the sensors 500 and 604 can measure amounts of consumables or levels of consumables that remain after any procedures and provide the remaining amounts and levels to the cart controller 110. The cart controller 110 can compare this amount to amounts that were present prior to procedures being performed, which would have been provided to the cart controller 110 as detailed above in anticipation of the upcoming procedures. The differences between the amounts can correspond to amounts used during the procedures. The cart controller 110 can pass this difference information along as billing data to the processor 906, which can be transmitted as billing data via the transceiver 900 to the server 802. The procedures during which the consumables were used can be associated with an entity, such as a patient, and the amount of consumables used can be billed to the patient in order to automatically create a bill for the patient.

As noted above, the cart controller 110 can include a procedure list stored in the memory 908. The procedure list can correlate consumables that are necessary for a particular procedure. Thus, when the smart cart 100 is assigned to a particular procedure, the cart controller 110 can automatically determine if the smart cart 100 includes the necessary instruments 320 and consumables for the procedure that are specific to the instruments. Moreover, the cart controller 110 can store information pertaining to a particular practitioner such as if a particular practitioner prefers a particular instrument. In these instances, not only can the cart controller 110 determine whether the smart cart 100 has the instrument preferred by the particular practitioner, the cart controller 110 can determine whether the correct consumables that are used with that particular instrument are stored on the smart cart 100.

While the workspace 112, the instrument hanger 108, the accessories 114, the accessories shelving 116, and the accessory 402 are described as being exposed, in further examples, the smart cart 100 can be fully enclosed. Here, the smart cart 100 can include a locking cabinet where the entire cart, with the exception of the display 102 and the handle 134, are secured within an enclosure.

In some instances, a procedure may require the user of two smart carts, such as the smart cart 100 and the smart cart 808C. Here, the while the smart cart 100 may be present in the area 814, the smart cart 808C may be present in a different area that is separate from the area 814. The smart cart 100 can communicate this to the user 810 when the user 810 enters the area 814. In particular, the server 802 can provide location data relating to the smart cart 808C to the smart 100, which can then provide the location data relating to the smart cart 808C to the user 810.

In further examples, the smart cart 100 can be configured to automatically provide consumables to a practitioner during a procedure. For example, the smart cart 100 can include a robotic arm that provide consumables to a practitioner during a procedure.

The smart cart 100 can be motorized to provide self-propelling functionality to the smart cart 100 where the user 810 can guide the smart cart 110 from one area such as the area 814, to another area, such as an operating room or a supply room for restocking of consumables and instruments. The smart cart 100 can include motors 1200 operatively coupled via motor output shafts 1202 to wheels 1204 of the smart cart 100. The motors 1200 can be a direct current (DC) motor, such as series DC motor, or any other type of high-torque DC motor.

Having described various aspects and features of the inventive subject matter, the following numbered examples are provided as illustrative embodiments:

Example 1 is a supply cart comprising: a transceiver that receives endoscope procedure data from a server; a processor that reads the procedure data and determines an instrument and consumables needed for a procedure associated with the procedure data; at least one sensor that determines a presence or absence of the instrument at the supply cart; and at least one indicator that provide an indication relating to the presence or the absence of the instrument at the supply cart.

In Example 2, the subject matter of Example 1 includes, an endoscopic instrument hanger including: a first sensor that determines a presence or absence of the instrument at the instrument hanger; and a first indicator that provides a first indication relating to the presence or the absence of the instrument at the instrument hanger.

In Example 3, the subject matter of Examples 1-2 includes, a second sensor that determines a presence or absence of the consumables at the supply cart; and a second indicator that provides a second indication relating to the presence or the absence of the consumables at the supply cart.

In Example 4, the subject matter of Examples 1-3 includes, a localization circuitry that: determines a location of the supply cart; creates location data based on the location of the supply cart; and provides the location data to the transceiver, wherein the transceiver transmits the location data to the server.

In Example 5, the subject matter of Examples 1-4 includes, wherein the procedure data indicates that the supply cart will be used for a first procedure and a second procedure, wherein: the processor determines that the first procedure requires a first instrument and the second procedure requires a second instrument different from the first instrument; the instrument sensor determines a presence or absence of the first instrument and the second instrument at the instrument hanger; and the first indicator that provides a third indication relating to the presence or the absence of the first instrument and the second instrument at the instrument hanger.

In Example 6, the subject matter of Examples 1-5 includes, wherein the procedure data indicates an object associated with the supply cart where the supply cart comprises a lighting feature that illuminates when the transceiver receives object data indicating that the object is proximate the supply cart.

In Example 7, the subject matter of Examples 1-6 includes, wherein one of the consumables corresponds to a fluid disposed within a container and the second sensor: measures a level of the fluid within the container; and provides the fluid level to the processor after the procedure.

In Example 8, the subject matter of Examples 4-7 includes, wherein the processor determines that the one of the consumables should be refilled based on the fluid level, wherein the processor causes the second indicator to show the absence of the one of the consumables.

In Example 9, the subject matter of Examples 5-8 includes, wherein the processor determines that the one of the consumables should be refilled based on the fluid level and comprising a display unit communicatively coupled with the processor wherein the processor causes a user interface to be displayed on the display unit in response to determining that the one of the consumables should be refilled.

In Example 10, the subject matter of Examples 4-9 includes, wherein the processor: associates the fluid level with an entity associated with the procedure; and provides billing data to the transceiver relating to the fluid level, wherein the transceiver transmits the billing data to the server.

In Example 11, the subject matter of Examples 1-10 includes, an accessories shelf; and a camera, the camera having a field of view that includes the accessories shelf and the instrument hanger.

Example 12 is a supply cart comprising: a transceiver that receives endoscope procedure data from a server; a processor that reads the procedure data and determines an instrument and consumables needed for a procedure associated with the procedure data; and an endoscopic instrument hanger including: a first sensor that determines a presence or absence of the instrument at the instrument hanger and if the instrument at the instrument hanger is sterilized; and a first indicator that provides a first indication relating to a sterilization status of the instrument at the instrument hanger.

In Example 13, the subject matter of Example 12 includes, a second sensor that determines a presence or absence of the consumables at the supply cart; and a second indicator that provides a second indication relating to the presence or the absence of the consumables at the supply cart.

In Example 14, the subject matter of Examples 12-13 includes, a localization circuitry that: determines a location of the supply cart; creates location data based on the location of the supply cart; and provides the location data to the transceiver, wherein the transceiver transmits the location data to the server.

In Example 15, the subject matter of Examples 12-14 includes, wherein the procedure data indicates that the supply cart will be used for a first procedure and a second procedure, wherein: the processor determines that the first procedure requires a first instrument and the second procedure requires a second instrument different from the first instrument; the instrument sensor determines a presence or absence of the first instrument and the second instrument at the instrument hanger; and the first indicator that provides a third indication relating to the presence or the absence of the first instrument and the second instrument at the instrument hanger.

In Example 16, the subject matter of Examples 12-15 includes, wherein the procedure data indicates an object associated with the supply cart where the supply cart comprises a lighting feature that illuminates when the transceiver receives object data indicating that the object is proximate the supply cart.

In Example 17, the subject matter of Examples 12-16 includes, wherein one of the consumables corresponds to a fluid disposed within a container and the second sensor: measures a level of the fluid within the container; and provides the fluid level to the processor after the procedure.

In Example 18, the subject matter of Example 17 includes, wherein the processor determines that the one of the consumables should be refilled based on the fluid level and wherein the processor causes the second indicator to show the absence of the one of the consumables.

In Example 19, the subject matter of Example 18 includes, wherein the processor determines that the one of the consumables should be refilled based on the fluid level and comprising a display unit communicatively coupled with the processor wherein the processor causes a user interface to be displayed on the display unit in response to determining that the one of the consumables should be refilled, wherein the processor: associates the fluid level with an entity associated with the procedure; and provides billing data to the transceiver relating to the fluid level, wherein the transceiver transmits the billing data to the server.

Example 20 is a supply cart comprising: a transceiver that receives endoscope procedure data from a server; a processor that reads the procedure data and determines an instrument and consumables needed for a procedure associated with the procedure data; an endoscopic instrument hanger including: a first sensor that determines a presence or absence of the instrument at the instrument hanger; and a first indicator that provides a first indication relating to the presence or the absence of the instrument at the instrument hanger; and a localization circuitry that: determines a location of the supply cart; creates location data based on the location of the supply cart; and provides the location data to the transceiver, wherein the transceiver transmits the location data to the server.

Example 21 is at least one machine-readable medium including instructions that, when executed by processing circuitry, cause the processing circuitry to perform operations to implement of any of Examples 1-20.

Example 22 is an apparatus comprising means to implement of any of Examples 1-20.

Example 23 is a system to implement of any of Examples 1-20.

Example 24 is a method to implement of any of Examples 1-20.

The above detailed description includes references to the accompanying drawings, which form a part of the detailed description. The drawings show, by way of illustration, specific examples in which the disclosure can be practiced. These examples are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the disclosure should be determined with reference to the appended claims, along with the full scope of equivalents to which such claims are entitled.

What is claimed is:

1. A supply cart comprising:

a transceiver receiving endoscope procedure data from a server;

a processor configured to read the endoscope procedure data and determine an instrument and one or more consumables needed for a procedure associated with the endoscope procedure data;

at least one sensor configured to determine a presence or absence of the instrument at the supply cart; and at least one indicator configured to provide an indication relating to the presence or the absence of the instrument at the supply cart.

2. The supply cart of claim 1, further comprising:

a localization circuitry configured to:

determine a location of the supply cart;

create location data based on the location of the supply cart; and provide the location data to the transceiver, wherein the transceiver is configured to transmit the location data to the server.

3. The supply cart of claim 1, wherein the endoscopic procedure data indicates an object associated with the supply cart, and wherein the supply cart comprises:

a lighting feature configured to illuminate when the transceiver receives object data indicating that the object is proximate the supply cart.

4. The supply cart of claim 1, further comprising:

an endoscopic instrument hanger including:

a first sensor configured to determine a presence or absence of the instrument at the endoscopic instrument hanger, the at least one sensor comprising the first sensor; and a first indicator configured to provide a first indication relating to the presence or the absence of the instrument at the endoscopic instrument hanger, at least one indicator comprising the first indicator.

5. The supply cart of claim 4, further comprising:

an accessories shelf; and a camera, the camera having a field of view that includes the accessories shelf and the endoscopic instrument hanger.

6. The supply cart of claim 4, wherein the endoscopic procedure data indicates that the supply cart will be used for a first procedure and a second procedure, wherein:

the processor is further configured to determine that the first procedure requires a first instrument and the second procedure requires a second instrument different from the first instrument;

at least one sensor is further configured to determine a presence or absence of the first instrument and the second instrument at the endoscopic instrument hanger; and the first indicator is further configured to provide a third indication relating to the presence or the absence of the first instrument and the second instrument at the endoscopic instrument hanger.

7. The supply cart of claim 1, further comprising:

a second sensor configured to determine a presence or absence of one or more consumables at the supply cart, at least one sensor comprising the second sensor; and a second indicator providing a second indication relating to the presence or the absence of one or more consumables at the supply cart, at least one indicator comprising the second indicator.

8. The supply cart of claim 7, wherein a first consumable of one or more consumables corresponds to a fluid disposed within a container and wherein the second sensor is configured to:

measure a level of the fluid within the container; and provide the level of the fluid to the processor after the procedure.

9. The supply cart of claim 8, wherein the processor is further configured to:

associate the level of fluid with an entity associated with the procedure; and provide billing data to the transceiver relating to the level of fluid, wherein the transceiver is configured to transmit the billing data to the server.

10. The supply cart of claim 8, wherein the processor is further configured to:

determine that the first consumable of one or more consumables should be refilled based on the level of the fluid; and cause the second indicator to show the absence of the first consumable of one or more consumables.

11. The supply cart of claim 8, wherein the supply cart further comprises a display unit communicatively coupled to the processor, and wherein the processor is further configured to:

determine that the first consumable of the one or more consumables should be refilled based on the level of fluid; and cause a notification on the user interface to be displayed on the display unit in response to determining that the first consumable of one or more consumables should be refilled.

12. A supply cart comprising:

a transceiver to receive endoscope procedure data from a server;

a processor;

memory, including instructions stored thereon that, when performed by the processor, cause the processor to:

read the endoscopic procedure data; and determine an instrument and one or more consumables needed for a procedure associated with the endoscopic procedure data; and an endoscopic instrument hanger including:

a first sensor to determine a presence or absence of the instrument at the endoscopic instrument hanger and whether the instrument at the endoscopic instrument hanger is sterilized; and a first indicator to provide a first indication relating to a sterilization status of the instrument at the endoscopic instrument hanger.

13. The supply cart of claim 12, further comprising:

a localization circuitry configured to:

determine a location of the supply cart;

create location data based on the location of the supply cart; and provide the location data to the transceiver, wherein the transceiver transmits the location data to the server.

14. The supply cart of claim 12, wherein the endoscopic procedure data indicates that the supply cart will be used for a first procedure and a second procedure, wherein:

the processor determines that the first procedure requires a first instrument and the second procedure requires a second instrument different from the first instrument;

the first sensor determines a presence or absence of the first instrument and the second instrument at the endoscopic instrument hanger; and the first indicator that provides a third indication relating to the presence or the absence of the first instrument and the second instrument at the endoscopic instrument hanger.

15. The supply cart of claim 12, further comprising:

a second sensor to determine a presence or absence of one or more consumables at the supply cart; and a second indicator to provide a second indication relating to the presence or the absence of one or more consumables at the supply cart.

16. The supply cart of claim 15, wherein a first consumable of one or more consumables corresponds to a fluid disposed within a container and the second sensor is configured to:

measure a level of the fluid within the container; and provide the level of fluid to the processor after the procedure.

17. The supply cart of claim 16, wherein the endoscopic procedure data indicates an object associated with the supply cart, and wherein the supply cart comprises a lighting feature to illuminate when the transceiver receives object data indicating that the object is proximate the supply cart.

18. The supply cart of claim 17, wherein the processor determines that the first consumable of the one or more consumables should be refilled based on the level of fluid, and wherein the instructions further cause the processor to:

cause the second indicator to show the absence of the first consumable of one or more consumables.

19. The supply cart of claim 18, wherein the supply cart further comprises a display unit communicatively coupled to the processor, and wherein the instructions further cause the processor to:

determine that the first consumable of one or more consumables should be refilled based on the level of fluid;

cause a user interface to be displayed on the display unit in response to determining that the first consumable of one or more consumables should be refilled;

associate the level of fluid with an entity associated with the procedure; and provide billing data to the transceiver relating to the level of fluid, wherein the transceiver is to transmit the billing data to the server.

20. A supply cart comprising:

a transceiver to receive endoscope procedure data from a server;

a processor to:

read the endoscopic procedure data; and determine an instrument and one or more consumables needed for a procedure associated with the endoscopic procedure data;

an endoscopic instrument hanger including:

a first sensor to determine a presence or absence of the instrument at the endoscopic instrument hanger; and a first indicator to provide a first indication relating to the presence or the absence of the instrument at the endoscopic instrument hanger;

a localization circuitry configured to:

determine a location of the supply cart;

create location data based on the location of the supply cart; and provide the location data to the transceiver, wherein the transceiver transmits the location data to the server.

* * * * *